(12) United States Patent
Brem et al.

(10) Patent No.: US 8,733,593 B2
(45) Date of Patent: May 27, 2014

(54) CARTRIDGE DISPENSER WITH ROTATIONAL LOCK

(75) Inventors: William Brem, Muri (CH); Andy Greter, Baar (CH)

(73) Assignee: Medmix Systems AG, Rotkreuz (CH)

( * ) Notice: Subject to any disclaimer, the term of this patent is extended or adjusted under 35 U.S.C. 154(b) by 0 days.

(21) Appl. No.: 13/806,016

(22) PCT Filed: Jun. 23, 2011

(86) PCT No.: PCT/CH2011/000152
§ 371 (c)(1),
(2), (4) Date: Dec. 20, 2012

(87) PCT Pub. No.: WO2012/006749
PCT Pub. Date: Jan. 19, 2012

(65) Prior Publication Data
US 2013/0087578 A1    Apr. 11, 2013

(30) Foreign Application Priority Data

Jul. 12, 2010    (CH) ........................................ 1131/10

(51) Int. Cl.
*B65D 83/00*    (2006.01)

(52) U.S. Cl.
USPC ........... 222/82; 222/326; 222/137; 222/145.5

(58) Field of Classification Search
USPC ......................................... 222/325, 386, 326
See application file for complete search history.

(56) References Cited

U.S. PATENT DOCUMENTS

| | | | | |
|---|---|---|---|---|
| 2,634,889 A | * | 4/1953 | Sherbondy | 222/327 |
| 3,997,085 A | * | 12/1976 | Lindquist | 222/326 |
| 4,869,400 A | * | 9/1989 | Jacobs | 222/137 |
| 5,018,768 A | * | 5/1991 | Palatchy | 285/24 |
| 5,184,757 A | * | 2/1993 | Giannuzzi | 222/82 |
| 5,336,014 A | | 8/1994 | Keller | |
| 5,992,694 A | | 11/1999 | Keller | |
| 6,047,864 A | | 4/2000 | Winkler | |
| 6,790,037 B1 | | 9/2004 | Orecchia | |
| 6,921,384 B2 | * | 7/2005 | Reilly et al. | 604/131 |
| 8,220,668 B2 | * | 7/2012 | Cadden et al. | 222/326 |
| 2008/0314929 A1 | | 12/2008 | Keller | |

FOREIGN PATENT DOCUMENTS

| | | | |
|---|---|---|---|
| WO | 2010/006455 A1 | | 1/2010 |
| WO | WO 2010006455 A1 | * | 1/2010 |
| WO | 2010/020060 A1 | | 2/2010 |

OTHER PUBLICATIONS

International Search Report of PCT/CH2011/000152 dated Sep. 21, 2011.

* cited by examiner

*Primary Examiner* — Paul R Durand
*Assistant Examiner* — Donnell Long
(74) *Attorney, Agent, or Firm* — Sughrue Mion, PLLC

(57) ABSTRACT

Proposed is a dispenser for discharging at least one flowable component from a cartridge. The dispenser comprises a cartridge holder (110) and an advancing element (120) that is slidable therein. A cartridge (200) can be axially inserted into the cartridge holder against a direction of advancing (V). In order to axially fix the cartridge, a rotating element (140) has been provided on the cartridge holder. In a first orientation the cartridge can be slid into the cartridge holder against the direction of advancing, while in the second orientation the rotating element axially fixes the inserted cartridge. Furthermore, in a third orientation the rotating element can be rotatable on the rotary axis in order to open at least one outlet opening of the cartridge.

21 Claims, 7 Drawing Sheets

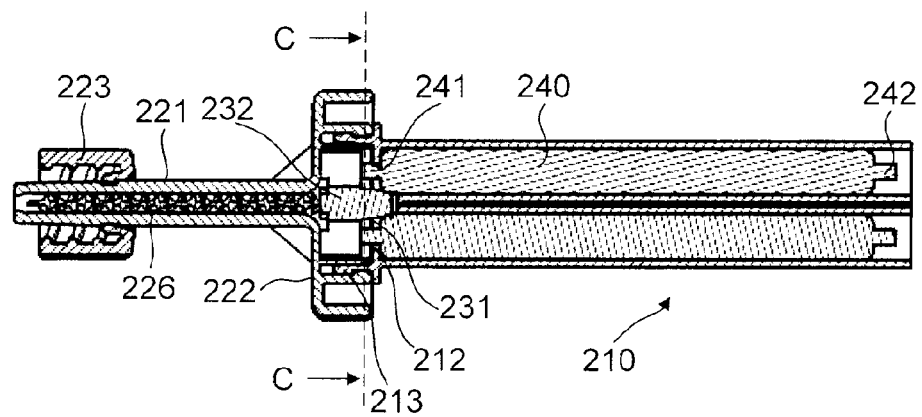
FIG. 15
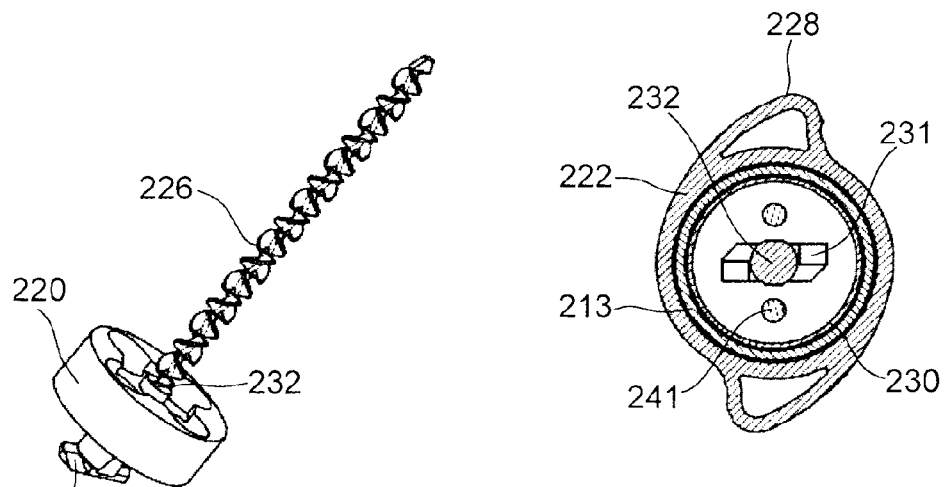
FIG. 16
FIG. 17

CARTRIDGE DISPENSER WITH ROTATIONAL LOCK

CROSS REFERENCE TO RELATED APPLICATIONS

This application is a National Stage of International Application No. PCT/CH2011/000152 filed Jun. 23, 2011, claiming priority based on Swiss Patent Application No. 01131/10, filed Jul. 12, 2010, the contents of all of which are incorporated herein by reference in their entirety.

TECHNICAL FIELD

The present invention relates to a discharging device for discharging at least one viscous substance from an exchangeable cartridge, which comprises at least one reservoir for a component to be dispensed. The component is dispensed from the reservoir by distal advancement of an advancing element along an axial direction of advancing. Hereinafter, such a discharging device is referred to as a "cartridge dispenser" or in an abbreviated manner simply as a "dispenser".

PRIOR ART

From the state of the art a multitude of different dispensers are known for pressing at least one highly-viscous component from a cartridge of the type mentioned above. In the use of such dispensers it is frequently necessary in relatively rapid succession to remove an empty cartridge and to insert a fresh cartridge. Such dispensers are used in a host of different fields and can correspondingly be designed and dimensioned in a host of different ways. For example, from the building industry so-called pistol dispensers for manually dispensing silicon sealants and other viscous building materials from cartridges by means of a slidable piston are known, which dispensers are in widespread use in that industry. Normally, in the above application the cartridge with the material to be dispensed is placed in the dispenser transversely to the direction of advancing of the piston.

However, dispensers are also in widespread use in the medical field in order to dispense viscous materials such as, for example, medical adhesives, dental compounds etc. One example of such a dispenser is disclosed in U.S. Pat. No. 6,790,037. A carpule-like cartridge comprising a dental compound is at the distal end of the dispenser placed into said dispenser transversely to the direction of advancing and by means of a rotating ring is secured against falling out. An advancing element in the form of a piston rod then advances a piston in the cartridge in the distal direction, thus expelling the sealing compound from the cartridge.

In many fields of application two or more components are to be dispensed simultaneously from syringe-like containers and are to be mixed only shortly before being used. Examples of this are, e.g., medical or non-medical two-component adhesives, bone cements or particular pharmaceutical products that are not storage-stable in the mixed state. For such applications various dispensers have been proposed that make it possible for two or more components to be dispensed simultaneously. One example of such a dispenser is disclosed in U.S. Pat. No. 5,336,014. In this dispenser a cartridge with two reservoirs, which in each case are delimited by a slidable piston, is placed in the dispenser in a direction that is transverse to the direction of advancing of the pistons. The cartridge is secured on the dispenser by means of a swivellable securing flap. By activation of an activation lever the components held in the reservoirs are simultaneously dispensed. A dispenser of a similar type has also been proposed in U.S. Pat. No. 5,992,694.

Furthermore, dispensers are known in which a cartridge is inserted axially in the dispenser, against the direction of advancement of the piston, from the distal end, and is secured on the dispenser. Such a dispenser is, for example, disclosed in U.S. Pat. No. 6,047,864. In this design the cartridge is held between flexible tongues that extend in the distal direction and that by means of a slidable sleeve can be secured in the radial direction. Since the tongues are subjected to bending loads, the selection of materials in such mechanisms is limited.

The components to be dispensed are frequently substances that are sensitive to air or humidity, aggressive substances or volatile substances. It is thus frequently necessary to enclose the substances in an airtight manner in their respective reservoirs until just before commencement of the discharging process, and to open the reservoirs only just prior to said discharging process. Normally, opening the reservoirs takes place manually prior to the cartridge being inserted in the dispenser. For this purpose, for example, pull-off seals are known, which in the storage state keep the outlet openings of the reservoirs closed, and which are pulled from the outlet openings just prior to use.

In US 2008/0314929 a cartridge is disclosed that comprises two reservoirs, each having a distal outlet opening. An accessory part, e.g. in the form of a mixer, is rotatably affixed to the distal end of the reservoir. The accessory part comprises two deformable plugs which in a first orientation of the accessory part close off the outlet openings of the two reservoirs. When the accessory part is rotated relative to the reservoirs, the plugs slide away from the outlet openings, thus opening them up. Such a cartridge can, if necessary, be placed in a suitable dispenser. Although such a cartridge can be opened very easily, the opening process nevertheless needs to take place separately of the process of insertion in the dispenser.

SUMMARY OF THE INVENTION

It is an object of the present invention to provide a discharging device for discharging at least one component from a cartridge, which discharging device makes it possible to insert the cartridge from the distal end axially into the dispenser, and to reliably affix said cartridge in a simple manner on the dispenser.

Thus, a discharging device for discharging at least one flowable component from a cartridge comprising at least one reservoir is provided. The discharging device comprises:
  a cartridge holder; and
  at least one advancing element that is mounted on the cartridge holder and that is adapted to be axially advanced relative to the cartridge holder along a distal direction of advancing, which advancing element is configured to act on the at least one reservoir of the cartridge in order to dispense from the reservoir a component received in the reservoir.

The cartridge holder is configured in such a manner that it is possible for the cartridge to be axially inserted (in particular, purely axially slid in) against the direction of advancing into the cartridge holder. For axially fixing the cartridge, the discharging device comprises a rotating element that is mounted on the cartridge holder and is axially secured relative to the cartridge holder and is rotatable between a first orientation and a second orientation about an (imaginary) rotary axis that extends along the direction of advancing. In the first orientation the rotating element makes it possible to axially insert the cartridge into the cartridge holder against the direction of advancing. In the second orientation the rotating element axially fixes the cartridge that has been inserted into the cartridge holder.

In this manner a very simple and fast cartridge exchange is made possible. In this arrangement the cartridge can be reliably connected to the cartridge holder in a very simple manner.

Hereinafter, the term "cartridge" refers to any unit that can be exchanged at will, which unit comprises at least one reservoir for a component that can be dispensed by the application of pressure. In particular, the cartridge can be designed in the manner of a single syringe or multiple syringe or carpule with one cylindrical reservoir or several cylindrical reservoirs, wherein the reservoirs are proximally limited in each case by a slidable piston or plug. However, alternative designs are also imaginable in which at least one reservoir is delimited for example by a bellows-like structure or by a flexible bag. Thus, the cartridge can, for example, basically be designed so as to be similar to that in WO 2010/006455 or WO 2010/020060. Irrespective of the concrete design of the cartridge, two or more reservoirs can jointly be connected to form a single inseparable unit, or one or several reservoirs can be detachably held in a cartridge housing from which the reservoirs can be removed individually. The reservoirs can also project beyond the cartridge housing. For example it is imaginable for one reservoir or several reservoirs to be inserted from the proximal end into a relatively short cartridge housing and to be held therein either removably or irremovably, wherein they project proximally beyond the cartridge housing. This is particularly possible when the reservoirs are designed in the manner of syringes or in the manner of carpules. Moreover, it is for example imaginable for the cartridge to comprise a relatively short, rigid cartridge housing to which one or several flexible, bag-shaped reservoirs have been attached, which reservoirs proximally project from the cartridge housing so that the advancing element can act on these reservoirs in order to press out the components held in the reservoirs. Preferably, the cartridge generally comprises an essentially rigid distal end region in order to in this region establish a non-rotational connection with the cartridge holder. Apart from the reservoirs, the cartridge can comprise further elements, for example an accessory part, either removably or irremovably connected to the reservoirs, in the form of a mixer or a spray attachment.

Correspondingly, the term "cartridge holder" refers to a device that is designed to at least in part receive a corresponding cartridge.

The present invention comprises a rotating element that is axially secured relative to the cartridge holder and that is rotatable about a rotary axis. Preferably the rotating element at least in the second orientation is axially essentially (i.e. apart from axial play inherent in the construction) non-displaceable, particularly preferably even in the entire region between the first orientation and the second orientation is axially essentially non-displaceable. However, it is also imaginable for the rotating element during its rotary movement from the first to the second orientation to be axially guided relative to the cartridge holder in such a manner that it experiences axial displacement, e.g. in order to proximally press the cartridge into the cartridge holder, thus reducing the play. In any case the rotating element is designed in such a manner that in the second orientation it prevents axial movement of the cartridge in the distal direction.

Preferably, the angular range between the first orientation and the second orientation is less than 90°, in particular preferably less than 60°. Axial locking of the cartridge in the cartridge holder can thus preferably be achieved by means of a comparatively small rotary movement.

The at least one reservoir of the cartridge preferably remains non-rotatable relative to the cartridge holder so that the reservoir is not taken along or at least not completely taken along by rotation of the rotating element from the first orientation to the second orientation. Preferably, to this effect the cartridge holder is rotationally asymmetrical in design, e.g. in that it comprises at least one tangential means of restraining the reservoir.

In preferred embodiments the rotating element is not only used for locking the cartridge to the cartridge holder, but also for opening the outlet opening of the at least one reservoir. To this effect the rotating element is preferably rotatable about the rotary axis relative to the cartridge holder to a third orientation. This third orientation differs from the first orientation and the second orientation; it is preferably reached by further rotation of the rotating element in the same direction of rotation as is the case during rotation from the first to the second orientation. In this case the rotating element preferably comprises at least one catch that is designed to take along into the third orientation a catching element of a cartridge held in the cartridge holder, in order to open at least one outlet opening of the cartridge.

Thus, by means of a simple rotary movement of the rotating element the cartridge can not only be fixed to the cartridge holder but can also be automatically opened by means of the same rotary movement. It is thus no longer necessary to manually open the outlet openings of the cartridge prior to insertion into the discharging device.

The advancing element can, in particular, comprise a piston rod that is designed to act on a piston that delimits the reservoir towards its proximal end. If the discharging device is designed to interact with a cartridge with several reservoirs arranged in parallel, the advancing element can also comprise two or more such piston rods, wherein these piston rods are then preferably interconnected at their proximal ends.

The discharging device can furthermore comprise the actual cartridge. In terms of possible designs of the cartridge, reference is made to the above elaborations.

The at least one reservoir is preferably affixable in the cartridge holder so as to be essentially non-rotational, as has already been stated above. To this effect the reservoir, or a cartridge housing connected to the reservoir, is preferably designed so as to be rotationally asymmetrical in relation to the rotary axis, and thus in this respect is complementary to the cartridge holder.

In order to axially affix the cartridge to the cartridge holder, the cartridge preferably comprises a retaining element. Relative to the at least one reservoir, the aforesaid is arranged on the cartridge so as to be axially secured in terms of the direction of advancing, preferably so as to be essentially non-displaceable. The rotating element is then designed in such a manner that in the first orientation it allows axial sliding of the retaining element into the rotating element. To this effect the rotating element in the first orientation opens up a cross-sectional area across the direction of advancing, which cross-sectional area in terms of its shape and size corresponds at least to the cross-sectional area of the retaining element. In the second orientation a locking region of the rotating element then establishes a positive-locking connection or a non-positive-locking connection with the retaining element in relation to the distal direction of advancing. In particular, the locking region can be at least one radially-inward projecting cam that in the second orientation covers a restraint region of the retaining element in the distal direction in order to in this manner establish positive locking with the retaining element.

Below, more detailed reference is made to a preferred alternative embodiment of the locking region as part of a mask-like design of a distal end wall of the rotating element.

The retaining element can be non-rotational or rotational relative to the reservoir. If it is rotational, relative to the reservoir, about the rotary axis of the rotating element, it is preferable for a predetermined retaining torque to have to be overcome before the retaining element is rotatable relative to the reservoir; this is to prevent the retaining element from being taken along during movement from the first orientation to the second orientation.

In order to open the at least one outlet of the at least one reservoir, the cartridge can, furthermore, comprise at least one catching element that is movable relative to the at least one reservoir, in particular rotatable about the rotary axis or slidable across the rotary axis. The catching element is arranged in such a manner that it can be taken along by the rotating element when the rotating element is rotated to the already mentioned third orientation.

In a first preferred embodiment a sealing plug for the outlet opening of the at least one reservoir is then connected directly or indirectly to the catching element, which sealing plug is removable from the outlet opening of the at least one reservoir by the movement of the catching element. To this effect the outlet opening of the at least one reservoir is preferably arranged so as to be offset to the rotary axis of the rotating element. The sealing plug can be designed so as to be deformable in such a manner that during movement of the catching element it deforms and slides from the outlet opening. The material and the dimensions of the sealing plug are then selected in such a manner that said sealing plug can be bent sufficiently far without being destroyed, preferably to a state in which the free end of each plug is deflected by up to 90° from its home position.

In particular, as far as the manner is concerned in which the outlets of the at least one reservoir are opened, the cartridge can be designed in the same manner as described in the already mentioned US 2008/0314929, whose content is completely incorporated into this document by reference.

In an alternative embodiment the at least one reservoir is designed as a flexible bag. In this case, preferably, at least one cutting element is associated with the catching element, which cutting element is arranged in such a manner that it cuts open the reservoir when the catching element is moved relative to the reservoir, in particular rotated on the rotary axis of the rotating element, or slid across the rotary axis. In terms of possible designs, reference is made in particular to the already mentioned documents WO 2010/006455 and WO 2010/020060, whose content is completely incorporated into this document by reference. In particular, the cutting element can comprise one or several blades whose cutting edges extend so as to be essentially perpendicular to the rotary axis of the rotating element, or it can comprise one or several blades whose cutting edges extend so as to be essentially parallel to, and spaced apart from, the rotary axis of the rotating element.

The catching element and/or the retaining element can be connected to an accessory part in the form of a mixer or a spray attachment, or it can form an integral part of such an accessory part. In a particularly simple embodiment, the catching element forms a rigid unit together with the retaining element. This unit can then be rigidly connected to the accessory part. The catching element can thus simultaneously also be used as a retaining element and vice-versa. In particular, the catching element and the retaining element can be designed in a single piece as one component.

In a preferred embodiment the rotating element comprises a distal end wall in which an insertion opening for the retaining element is formed, which insertion opening is rotationally asymmetrical relative to the rotary axis. This insertion opening can be designed in the manner of a mask that circumferentially is delimited by the end wall. This makes it immediately recognizable to a user as to the orientation in which the retaining element is to be inserted. The retaining element then comprises a shape that is complementary to the shape of the insertion opening, wherein this shape has been selected in such a manner that the retaining element in the first orientation can be slid through the insertion opening into the rotating element, and that subsequent rotation of the rotating element relative to the retaining element into the second orientation causes interaction of the retaining element with the end wall so that the end wall prevents sliding of the retaining element in the distal direction. In particular, the retaining element itself can also comprise a distal end wall, wherein the distal end wall of the rotating element in the second orientation then covers the distal end wall of the retaining element at least in part.

The cartridge can, in particular, be a cartridge for discharging at least two components. To this effect the cartridge comprises at least two reservoirs that are arranged so as to be parallel to each other. In the region of its respective distal end each of the reservoirs then comprises an outlet opening (preferably arranged so as to be offset to the rotary axis of the rotating element) or (in the case of closed bags) an outlet region for forming such an outlet opening. The reservoirs can be interconnected in a rigid manner, in particular in a single piece; however, the reservoirs can also be designed separately, jointly held in a cartridge housing. In a preferred embodiment the two reservoirs are at least in part delimited by a shared cartridge housing, wherein this housing is not rotationally symmetrical in design.

The rotation range of the rotating element is preferably limited. In particular, it is advantageous if the rotation range is limited to less than 180°. In this manner it is possible to effectively prevent a user from inserting a cartridge in an orientation of the rotating element, which orientation does not correspond to the first orientation. In order to limit the rotation range, the rotating element can comprise at least one stop element that interacts with the cartridge holder in order to limit the rotation range. The stop element can, in particular, be a stop cam that travels in a guideway of the cartridge holder, wherein the guideway on both sides in circumferential direction comprises a stop for the stop cam. Of course, the roles of the stop cam and of the guideway could also be reversed so that a guideway is formed on the rotating element, in which guideway a stop cam of the cartridge holder travels. Of course, other means are also known in order to limit the rotary movement of a rotating element on both sides to a specified angular range.

Preferably, the rotating element is arranged on the distal end of the cartridge holder and limits a distal insertion opening for the cartridge. In a preferred embodiment, in the region of the distal end of the cartridge holder there is a retaining flange that protrudes radially and is at least partially circumferential. The rotating element comprises two half-shells that have been slid onto the retaining flange across the direction of advancing and that are interconnected. In order to radially fix the half-shells the rotating element can comprise a fixing ring that has been non-rotatably connected to the half-shells, in particular axially slid onto the half-shells.

Between the cartridge holder and the rotating element a restraining device can be arranged, which results in rotation of the rotating element relative to the cartridge holder requiring a particular torque threshold to be overcome. In this manner unintended rotation of the rotating element relative to the cartridge holder is prevented. The restraining device can, for example, comprise an O-ring that causes increased friction between the cartridge holder and the rotating element. As an alternative, a ratchet connection, for example in the form of a symmetrical or asymmetrical inclined tooth arrangement, can be provided between the cartridge holder and the rotating element.

The discharging device can, furthermore, comprise a handgrip that extends essentially across the direction of advancing. In a particularly simple design the handgrip is designed in such a manner that it can be held by at least two fingers of one hand of a user, preferably with the index finger, middle finger, ring finger and the small finger. During use as intended, the index finger is preferably on a first (upper) radial side of the cartridge holder, while the remaining three fingers mentioned are situated on the other (lower) side of the cartridge holder. At the proximal end of the advancing element, preferably a ball-of-the-thumb support is designed in such a manner that by means of the ball of the same hand with which the user holds the handgrip said ball support can be advanced in the distal direction. In this manner very simple single-handed dispensing of the components from the reservoir or reservoirs is made possible. Of course, the discharging device can also be designed in some other manner; for example it can comprise mechanical means in order to generate a lever effect as is known from various embodiments from the state of the art. For example, the discharging device can also be designed in the manner of a pistol dispenser, which is known per se.

BRIEF DESCRIPTION OF THE DRAWINGS

Below, preferred embodiments of the invention are described with reference to the drawings, which are merely provided for clarification and are not to be interpreted as being limiting. The following are shown in the drawings:

FIG. 15 a central longitudinal section of the assembled cartridge of FIG. 14;

FIG. 16 an enlarged perspective view of a mixing element with an opening element affixed thereto; and FIG. 17 a cross section of the cartridge of FIG. 15 in the plane C-C.

DESCRIPTION OF PREFERRED EMBODIMENTS

Figure 1:
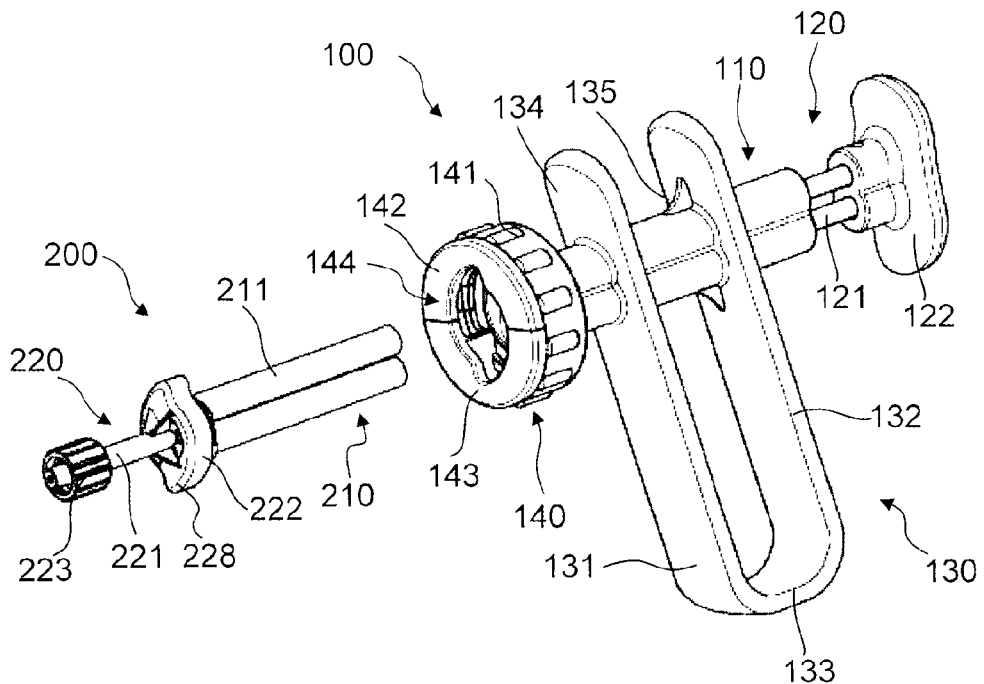
FIG. 1 a perspective view of a cartridge dispenser according to the invention with an associated cartridge according to a first embodiment.
Figure 2:
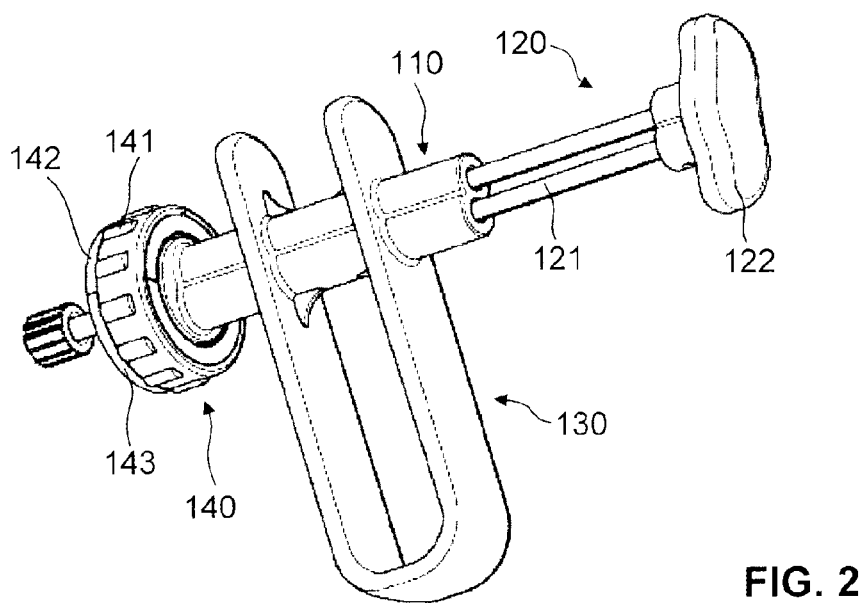
FIG. 2 a perspective view of the cartridge dispenser of FIG. 1, after insertion of the cartridge into the dispenser.

FIGS. 1 to 13 illustrate a first exemplary embodiment of a discharging device according to the invention in various views. Hereinafter, this discharging device is referred to as a "cartridge dispenser" or in an abbreviated manner simply as a "dispenser".

The dispenser 100 comprises a cartridge holder 110 which with a housing 111 forms two cylindrical hollow spaces, arranged parallel to each other and interconnected by their jacket surfaces, for receiving two reservoirs 211 of a cartridge 200. From the rear (proximal) end two piston rods 121 of an advancing element 120 extend into the cylindrical hollow spaces of the cartridge holder 110. At their proximal ends the piston rods 121 are connected by way of an advancement flange 122 in the form of a ball-of-the-thumb support. The advancing element 120 can be advanced relative to the cartridge holder 110 along a distal direction of advancing V (see FIG. 3).

A U-shaped handgrip 130 with a first leg 131, a second leg 132 and a connecting region 133 that connects the legs is rigidly connected to the cartridge holder 110. In this arrangement the legs 131, 132 extend essentially across the direction of advancing, at an angle of approximately 110° to this direction. In this arrangement the cartridge holder 110 is incorporated in the two legs 131, 132 of the handgrip 130 in such a manner that the legs, in a protruding region 134 on the side of the cartridge holder 110 which side is opposite the connecting region 133, project beyond the cartridge holder 110. Stabilising webs 135 stabilise the handgrip vis-à-vis shear forces that can occur during handling of the discharging device.

Figure 3:
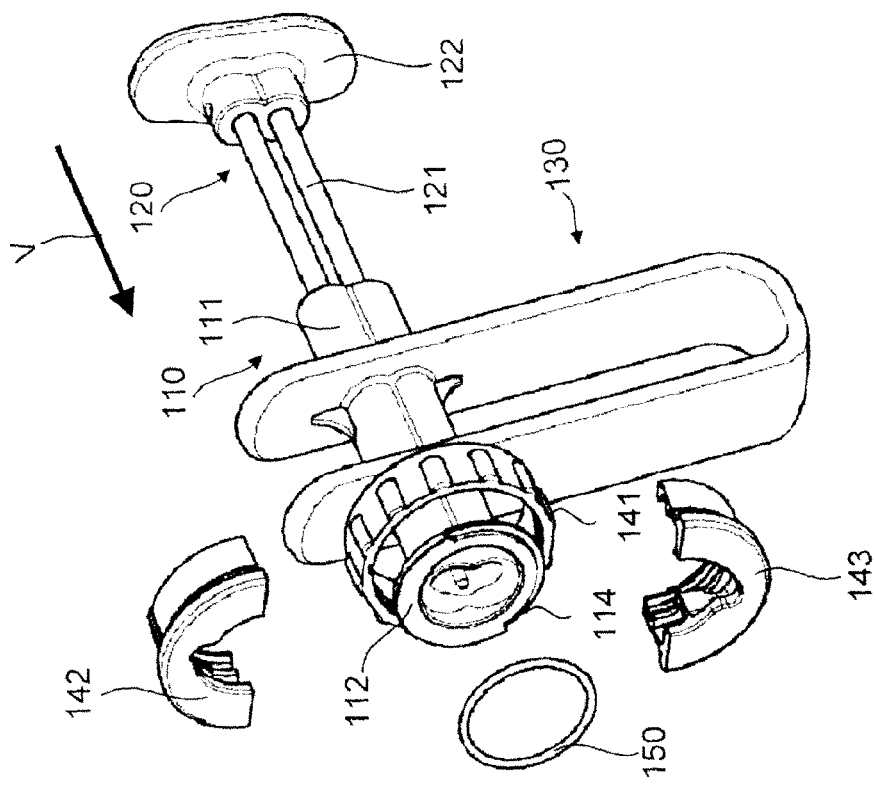
FIG. 3 a perspective disaggregated component view to illustrate the design of the distal end of the cartridge dispenser.
Figure 3:
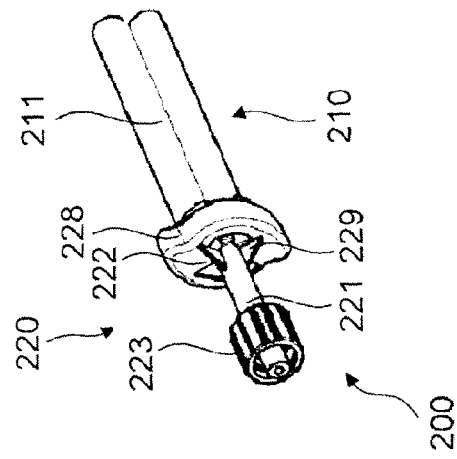
Figure 4:
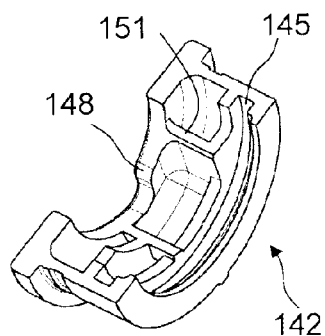
FIGS. 4 and 5 in each case a half-shell of a rotating element of the cartridge dispenser.
Figure 5:
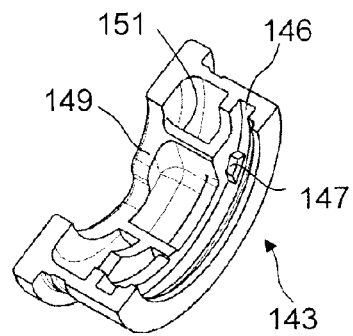
Figure 10:
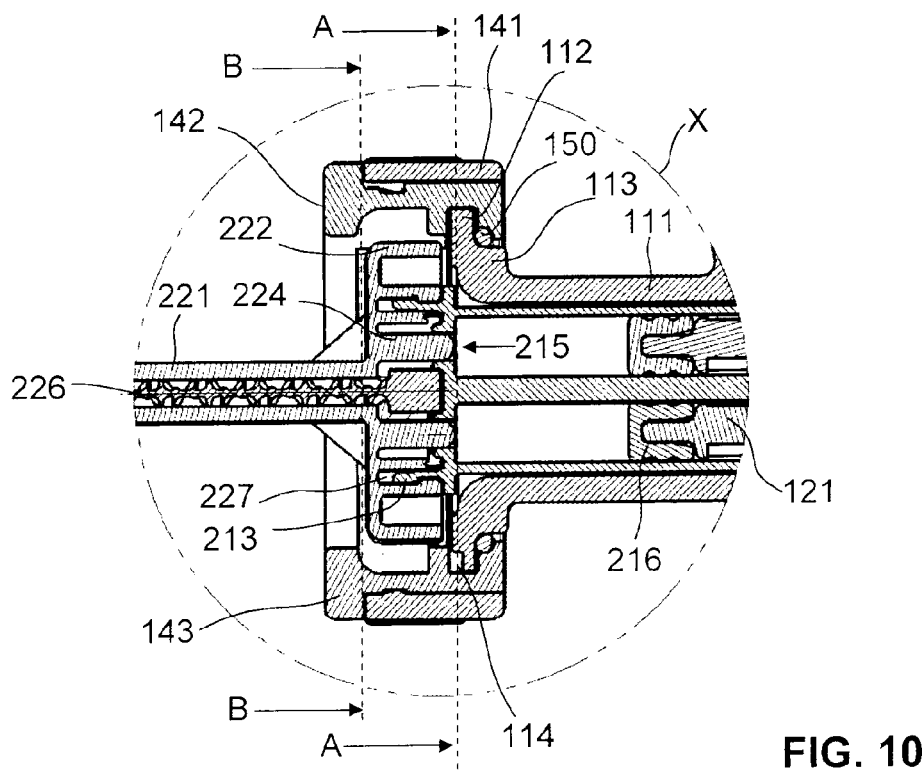
FIG. 10 an enlarged detailed view of detail X of FIG. 9.
Figure 11:
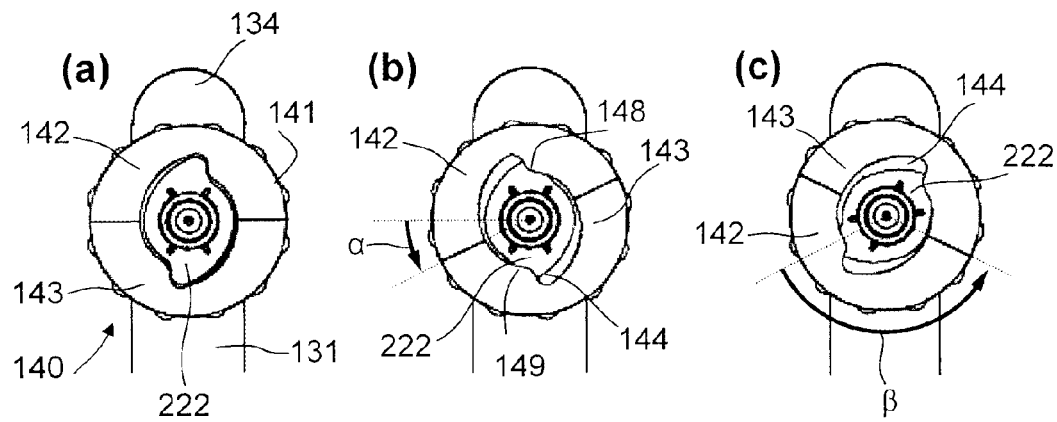
FIG. 11 a front view of the cartridge dispenser with a cartridge inserted, in a (a) first, (b) second and (c) third orientation of the rotating element.

As is shown, in particular, in FIGS. 3 and 10, the cartridge holder 110 at its distal end comprises an essentially circular retaining flange 112 that projects radially from the housing 111 and circumferentially encloses the housing 110. An upper half-shell 142 and a lower half-shell 143 of a rotating element 140 have been placed radially from opposite sides onto the retaining flange 112 and have been radially fixed, by a rotating ring 141 slid on axially from the proximal end along the direction of advancing, to the half-shells. In this arrangement the retaining flange 112 engages corresponding guiding grooves 145, 146 of the half-shells 142, 143, which are shown particularly clearly in FIGS. 4 and 5. An O-ring 150 has been slid onto a step-like circumferential recess 113 of the retaining flange 112 from the proximal end (compare FIGS. 3 and 10) and is affixed on the recess 113 by the two half-shells 142 and 143. In this arrangement the half-shells 142, 143 slightly compress the O-ring so that when the rotating element 140 is rotated in the circumferential direction the O-ring generates defined frictional force between the retaining flange 112 and the half-shells 142, 143.

At their distal ends the two half-shells 142, 143 circumferentially delimit a receiving aperture 144 that is complementary to the cross sectional shape of a retaining element 222 of the cartridge, which retaining element 222 will be described in more detail below, through which receiving aperture 144 the retaining element 222 can be axially inserted, in the proximal direction, into the rotating element 140. In the present embodiment the receiving aperture 144 is not rotationally symmetrical in design, but symmetrical relative to rotation by 180° ("two-fold symmetry"). Of course, completely asymmetrical forms or forms of some other symmetry are also possible.

Figure 12:
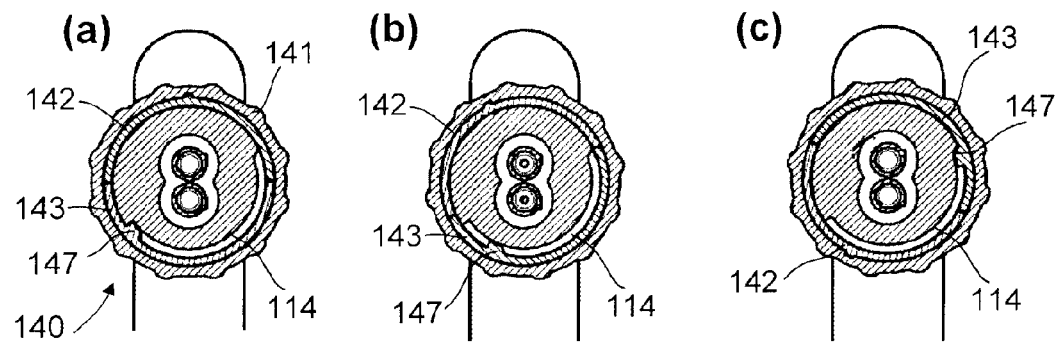
FIG. 12 a cross section of the cartridge dispenser with a cartridge inserted, in the plane A-A in the first, second and third orientation.
Figure 13:
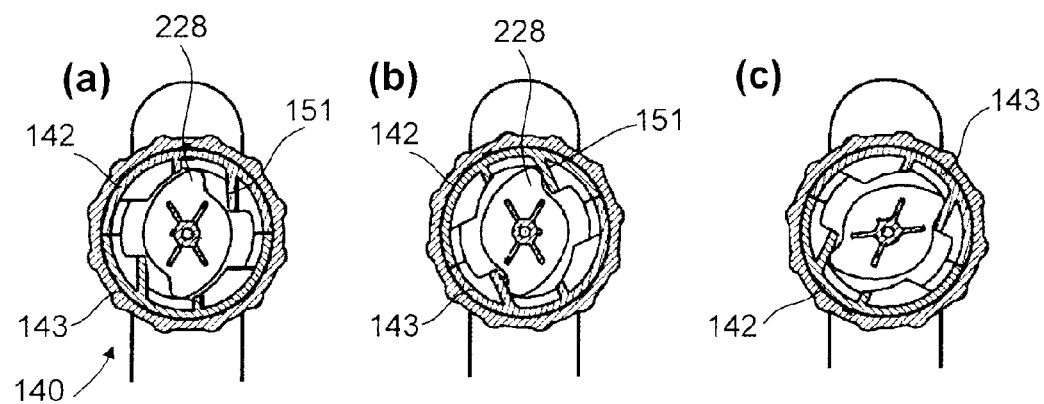
FIG. 13 a cross section of the cartridge dispenser with a cartridge inserted in the plane B-B.
Figure 14:
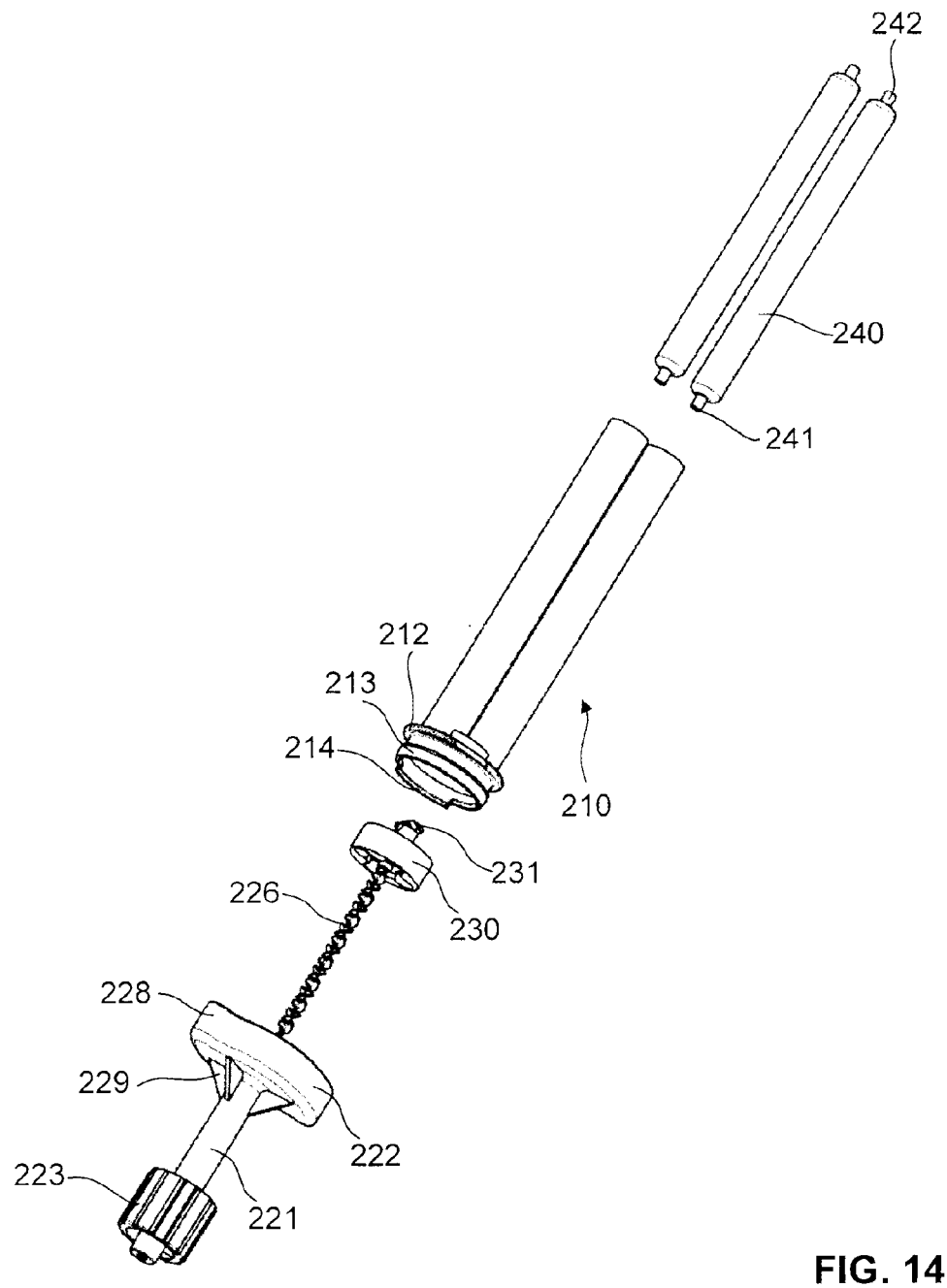
FIG. 14 a perspective disaggregated component view of a cartridge according to a second embodiment.

In the guiding groove of the lower half-shell 143 a stop cam 147 is formed that runs in a guideway 114 of the retaining flange 112 (cf. FIGS. 3 and 12). As a result of this design the rotating element 140 is rotatable over a defined angular range relative to the cartridge holder 110. In this arrangement the length of the guideway 114 and the dimensions of the stop cam 147 are selected in such a manner that the region by which the rotating element is rotatable is limited to approximately 160°. In cooperation with the two-fold symmetry of the receiving aperture 144 and the design, to be described below, of the cartridge, in this manner it is ensured that there is only precisely one orientation of the rotating element 140 (hereinafter referred to as the "first orientation") in which the cartridge can be inserted into the cartridge holder 110. As a result of the friction with the O-ring 150, the rotary movement of the rotating element 140 is restrained as long as the torque produced by a user on the rotating element 140 relative to the cartridge holder 110 does not exceed at least a certain torque threshold. In this manner, unintended rotation of the rotating element 140 is effectively prevented.

Figure 6:
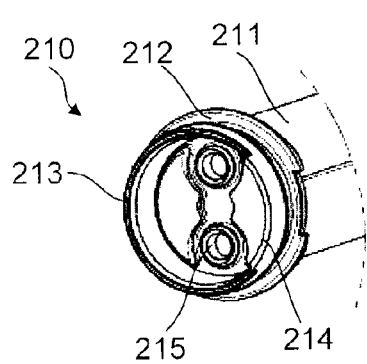
FIG. 6 a perspective partial view of the distal end of the cartridge housing with the accessory part removed.
Figure 7:
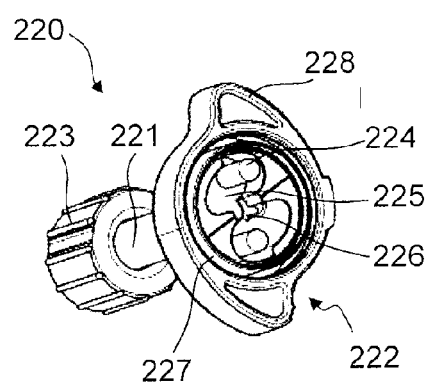
FIG. 7 a perspective view of the accessory part to illustrate the closures of the reservoir of the cartridge.
Figure 8:
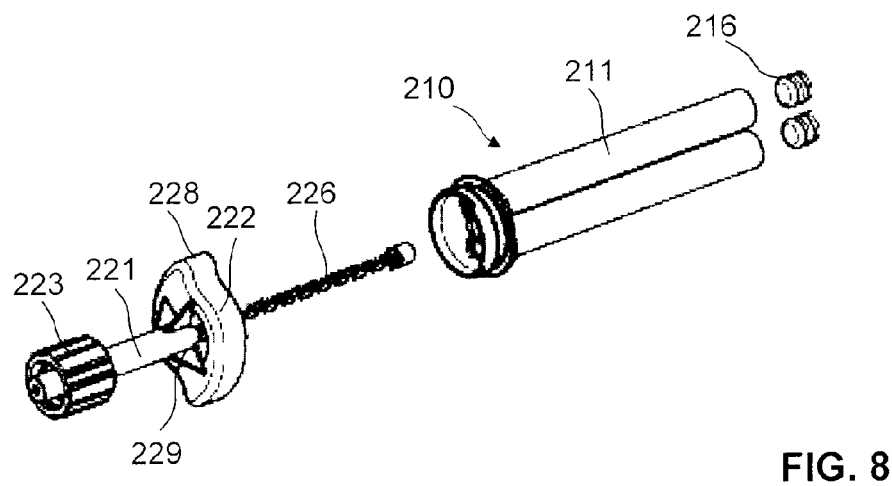
FIG. 8 a perspective disaggregated component view of the cartridge.
Figure 9:
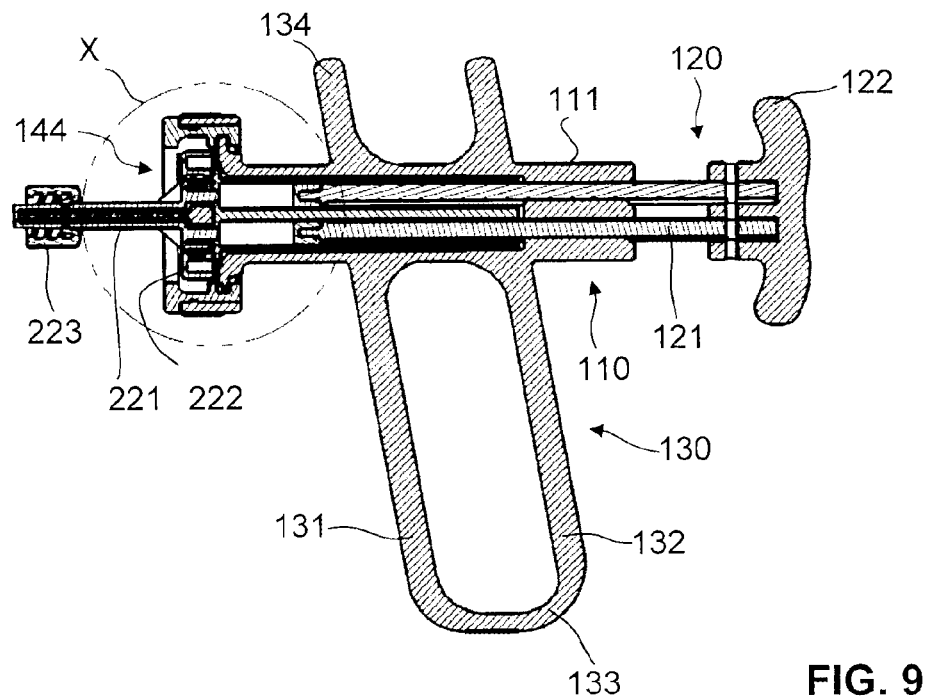
FIG. 9 a central longitudinal section of the cartridge dispenser with a cartridge inserted.

The cartridge 200 is shown in detail in particular in FIGS. 6 to 8. The cartridge comprises a cartridge housing 210 that delimits two parallel cylindrical reservoirs 211. At each of their respective distal ends the reservoirs 211 comprise an outlet opening 215 that is arranged off-centre relative to the rotary axis of the rotating element 140. At each of their proximal ends the reservoirs are closed off by a slidable piston 216. At their distal ends the reservoirs are interconnected by way of an essentially circular retaining plate 212. A snap-on region 213 in the shape of a partial ring extends from the retaining plate 212 in the distal direction and at its distal end comprises a snap-on rim that projects radially outwards. In a circumferential region the snap-on rim comprises an axial projection 214.

An accessory part 220 has been snapped into place on the cartridge housing 210. The accessory part 220 comprises a mixing tube 221 that together with a helical mixing element 226, which is known per se, forms a static mixer. The distal mixer outlet of the mixing tube 221 comprises a male Luer connection with a coupling sleeve 223, which is known per se. In this region it is possible, for example, for a cannula or a catheter to be connected to the mixer outlet.

At its proximal end region the mixing tube 221 is connected to a retaining element 222 that can be snapped onto the snap-on region 213 of the cartridge housing 210. The retaining element 222 radially projects beyond the cartridge housing 210. For stabilisation, a multitude of stabilising webs 229 have been provided between the mixing tube 221 and the retaining element 222.

The retaining element 222 forms an inlet chamber for the components, which inlet chamber is open towards the proximal end and is laterally delimited by a jacket wall of the retaining element, before said components enter the mixing tube 221. In this inlet chamber two flexible plugs 224 are arranged. Adjacent to the plugs, indentations 225 are arranged that are dimensioned in such a manner that they receive the plugs 224 when said plugs 224 are bent over in the circumferential direction. In order to make it possible to achieve such deformation of the plugs, the retaining element 222 together with the plugs 224 and with the mixing tube 221 are made in a single piece from a sufficiently flexible and tenacious material, e.g. a suitable polyethylene (PE) or polypropylene (PP). As an alternative, the plugs can be made from some other material that differs from that of the remainder of the retaining element 222, e.g. in a two-component injection-moulding process. The jacket wall of the retaining element comprises a circumferential connecting groove 227. In order to establish a connection of the accessory part 220 with the cartridge housing 210, the snap-on region 213 can be axially inserted into the connecting groove 227, after which the snap-on rim of the snap-on region 213 engages a corresponding undercut in the connecting groove 227. In this manner the accessory part 220 is secured in the axial direction on the cartridge housing 210 and is sealed relative to the cartridge housing 210 while being rotatable relative to the cartridge housing 210. The axial projection 214 of the snap-on region 213 projects more deeply into the connecting groove 217 than does the remaining snap-on region. The projection interacts in the circumferential direction with two stops (not shown in the drawings) in the connecting groove 227 in order to limit the angular region along which rotation of the accessory part 220 relative to the cartridge housing 210 is possible. The connection between the cartridge housing 210 and the accessory part 220 is made in such an orientation that the plugs 224 extend into the outlet openings 215 of the reservoirs 211, thus closing said outlet openings 215.

The retaining element 222 has a cross section that is rotationally asymmetrical and in the present embodiment approximately assumes the shape of a stylized "S". Consequently the retaining element 222 forms two radially-projecting catching regions 228.

In order to dispense from the cartridge the components received in the reservoirs 211, and in order to mix them in the mixing tube 221, first the cartridge 200 is axially inserted, against the direction of advancing V, into the cartridge holder 110. In this process the rotating element 140 assumes the first orientation, which is shown in FIG. 11(a). In this orientation the retaining element 222 with its catching elements 228 and the distal opening that is limited by the half-shells 142, 143 are oriented relative to each other in such a manner that the retaining element can be slid into the rotating element 140.

As soon as the cartridge 200 has reached its proximal end position in the cartridge holder, the user rotates the rotating element 140 counterclockwise by an angle α, as illustrated in FIG. 11(b). In this arrangement the retaining element 222 of the cartridge at first remains non-rotational so that the asymmetrical shape of the retaining element and the asymmetrical shape of the insertion opening are no longer aligned to each other. Consequently, locking regions 148, 149 (compare also FIGS. 4 and 5) of the distal end wall of the rotating element 140 on the distal end come to rest axially in front of the retaining element 222, thus fixing said retaining element 222 relative to movements of the cartridge in the distal direction. More abstractly expressed, the locking regions 148, 149 of the distal end wall of the rotating element, which locking regions 148, 149 overlap the retaining element 222, can also be considered to be a type of retaining cam of the rotating element 140, which retaining cams establish positive-locking engagement with the retaining element 222. In this arrangement it is, in principle, also imaginable for such retaining cams not to come to rest in front of a distal end wall of the retaining element 222, but instead, for example, to engage a radial groove of the retaining element 222.

The rotating element 140 is thus rotatable relative to the cartridge holder 110 by an angle of rotation a from a first orientation to a second orientation. In the first orientation the cartridge can axially be inserted against the direction of advancing into the cartridge holder 110, while the cartridge 200 inserted in this manner is axially fixed in the second orientation. In the present example the angle of rotation a between the first orientation and the second orientation is approximately 25°, but it can also be selected so as to be greater or smaller. In order to achieve secure fixing, the angle of rotation should, however, comprise at least approximately 15°.

As shown in FIG. 13(b), in the second orientation two catches in the form of catch webs 151 relative to the direction of rotation tangentially rest against the catching elements 228 of the retaining element 222. With further counter-clockwise rotation of the rotating element, the rotating element 140 therefore takes along the retaining element 222. Since as a result of their shape the reservoirs 211 are non-rotatably fixed in the cartridge holder 110 this results in rotation of the retaining element 222 relative to the reservoirs 211. Consequently the plugs 224 slide from the outlet openings 215 and are bent in the circumferential direction in such a manner that they are received in the indentations 225 so as to be essentially parallel to the circumferential direction. Consequently the outlet openings 215 of the reservoirs 211 are opened.

This situation is illustrated in FIG. 11(c), FIG. 12(c) and FIG. 13(c). In these illustrations the rotating element 140 was rotated onwards by a further angle of rotation β beyond the second orientation into a third orientation. In the present example the angle of rotation β is approximately 130°, but again it can be selected so as to be greater or smaller. In the present example an angle of rotation β of at least approximately 90° is advantageous.

As shown in FIGS. 12(a)-(c), further rotation of the rotating element 140 is prevented in that the stop cam 147 has arrived at the end of the guideway 114, thus relative to the circumferential direction striking against the retaining flange 112. This effectively prevents further rotation of the rotating element 140, which rotation might result in destroying the connection between the cartridge housing 210 and the accessory part 220. As shown in FIG. 12(a), the rotation range is also limited in the opposite direction by interaction between the stop cam 147 and the retaining flange 112. Overall, the rotation range of the rotating element between the first orientation and the third orientation is thus limited to a range of approximately 160°. As already mentioned, it is also possible to select a larger or a smaller range. A range of approximately 105° to approximately 170° is preferable. In the present two-fold symmetry a range of less than 180° prevents the cartridge from being inserted in an orientation other than the first orientation of FIGS. 11(a), 12(a) and 13(a). In contrast to this, when the insertion opening 144 is not axially symmetrical, it is sufficient for the rotation range to be limited to less than 360°.

In the third orientation the outlet openings 215 of the reservoirs 211 are open, and by advancement of the advancing element 120 in the distal direction the components can be dispensed from the reservoirs 211 and mixed in the mixing tube 221.

To this effect, in the present example the dispenser is held in one hand, wherein the index finger comes to rest between the two projecting regions 134 of the legs 131, 132, while the middle finger, the ring finger and the small finger come to rest against the handgrip between the cartridge holder 110 and the connecting region 133. With the ball of the thumb of the same hand the user can then exert pressure onto the advancement flange 122 in order to advance the two piston rods 121, thus inserting the pistons 216 into the cartridge housing 210.

In order to exchange the cartridge, the rotating ring 140 is turned back clockwise by the angle α. In this process, because of frictional forces, the retaining element 222 remains non-rotational relative to the cartridge housing 210. In this manner the insertion opening 144 is again made to coincide with the retaining element 222 so that the cartridge can distally be withdrawn from the cartridge holder 110. In order to insert a new cartridge, subsequently the rotating ring is rotated back to its home position (i.e. to the first orientation).

While in this document the invention has been illustrated with reference to a preferred exemplary embodiment, the invention is not at all limited to the present exemplary embodiment, and a multitude of modifications are possible. Thus, the dispenser can, in particular, also be of some type of dispenser other than the type shown, e.g. a so-called pistol dispenser as has been known for a long time from the state of the art. In such pistol dispensers, by lever action, a reduction ratio between an activation movement of the user and the advancement movement of the advancing element is generated, and consequently greater force acting on the advancing element can be generated than is possible in a simple dispenser of the type shown in the present drawings.

The cartridge can also be opened in a manner that differs from that shown in the present document. It is, for example, imaginable for a catching element of the cartridge to be designed so as to be separate of the retaining element. Such a catching element could, for example, convert a movement of a catch of the rotating element, which movement is tangential to the direction of rotation, to an axial movement of the sealing plugs so that the plugs would be axially pulled from the openings. This could, for example, take place by way of suitable inclined faces that are inclined towards the tangential direction in the direction of advancing. It would still be possible to axially secure the cartridge to the cartridge holder by a simple rotary movement, and to open the reservoirs in a very simple manner by means of the same rotary movement. Of course, a multitude of further embodiments are possible.

Instead of providing two reservoirs it is also possible for only a single reservoir, or for three or more reservoirs, to be provided. Instead of providing a mixer, some other unit acting as an accessory part can be provided on the cartridge, e.g. a spray attachment. Such a unit can be removably affixable to the retaining element, or can be omitted entirely.

An alternative embodiment of a cartridge is illustrated in FIGS. 14-17. Identical parts or parts with identical functions have the same reference characters as in FIGS. 1-13. In this embodiment the reservoirs are designed as elongated bags 240 that are essentially cylindrical. At the front, distal, end each bag comprises a tapered outlet region 241. The proximal, rear end 242 of each bag is designed so as to be complementary to the form of the distal end (not shown) of the advancing element 120 in order to ensure controlled axial advancement.

The bags 240 have been slid from the proximal side into a cartridge housing 210 that delimits two parallel cylindrical receiving regions for the bags. In this arrangement the outlet regions 241 of the bags project distally through the openings of the retaining plate 212.

In this exemplary embodiment the mixing element 216 is rigidly connected to a ring-shaped carrier 230, which essentially can be slid with a perfect fit but rotatably from the distal side to that region of the cartridge housing which region is radially delimited by the snap-on region 213. In the proximal direction, a carrier shaft 232 axially projects from the carrier, with a cutting element 231 comprising two diametrically opposed radially-outwards-extending blades being attached to the proximal end of said carrier shaft 232.

In the assembled state of the cartridge a non-rotational connection exists between the retaining element 222 and the carrier 230 so that the carrier 230 and thus also the cutting element 231 during rotation of the retaining element 222 relative to the cartridge housing 210 are carried along on the rotary axis. In this process the blades of the cutting element 231 cut the outlet regions 241 of the two bags 240, and consequently the fluids held in the bags 240 can reach the inlet chamber for the mixing tube 221, which inlet chamber is delimited by the retaining element 222.

Operating the dispenser takes place in the same manner as in the first exemplary embodiment. Here again, the cartridge is axially inserted in the first orientation into the dispenser, and by rotation of the rotating element 140 is fixed to the second orientation. The reservoirs are opened in that the rotating element 140 is rotated from the second orientation to the third orientation. In this rotation the retaining element 222 is again taken along by the rotating element 140. In this process the carrier 230, as described above, is rotated relative to the cartridge housing 210, and consequently the cutting element cuts open the bags 240.

Here, too, a multitude of modifications are possible. For example, the blades of the cutting element 231 can also extend so as to be parallel to the rotary axis in order to cut a correspondingly arranged delimitation wall of the bags. The bags can proximally project beyond the cartridge housing 210 so that when the cartridge has been inserted they rest directly against the walls of the cartridge holder 110. To this effect the cartridge housing 210 can be designed so as to be very short so that in the proximal direction it extends just far enough into the cartridge holder 110 to provide an anti-rotation lock between the cartridge 200 and the cartridge holder 110. The two bags 240 can be interconnected along a shared connecting line. To this effect it is imaginable for the cartridge housing 210 to form only one single, correspondingly large, receiving region for the two bags 240. The ends of the bags can also be designed in a manner that differs from that shown in the present document. In particular, it is imaginable that the bags are closed at the proximal end by means of a straight weld seam. As is the case in the first exemplary embodiment, the cartridge can, in addition, comprise pistons 216 for exerting pressure on the bags for squeezing them. Of course, it is also possible for only a single bag to be provided, or for three or more bags to be provided.

The invention claimed is:

1. A discharging device for discharging at least one flowable component from a cartridge comprising at least one reservoir, comprising:
   a cartridge holder;
   at least one advancing element that is mounted on the cartridge holder and that is adapted to be axially advanced relative to the cartridge holder along a distal direction of advancing, which advancing element is configured to act on the at least one reservoir of the cartridge in order to dispense from the reservoir a component received in the reservoir;
   a cartridge with at least one reservoir for a component, wherein the reservoir is configured in such a manner that the component can be dispensed from the at least one reservoir through an outlet opening by distal advancement of the advancing element, the at least one reservoir being fixable in the cartridge holder so as to be essentially non-rotational, the cartridge comprising a retaining element that relative to the at least one reservoir is axially secured in terms of the direction of advancing;
   at least one catching element that is movable relative to the at least one reservoir;
   a rotating element that is mounted on the cartridge holder and is axially secured relative to the cartridge holder and is rotatable at least between a first orientation and a second orientation about a rotary axis that extends along the direction of advancing, wherein in the first orientation the rotating element makes it possible to axially insert the cartridge into the cartridge holder against the direction of advancing, allowing axial sliding of the retaining element into the rotating element, and wherein the rotating element is configured to axially fix the cartridge inserted into the cartridge holder when it is in the second orientation, comprising a locking region which in the second orientation of the rotating element establishes a positive-locking connection or a non-positive-locking connection with the retaining element in relation to the distal direction of advancing; and
   at least one sealing plug for the outlet opening of the at least one reservoir,
   wherein the catching element is configured to be taken along by the rotating element when the rotating element is rotated to a third orientation, which differs from the first orientation and the second orientation, in order to open the at least one reservoir, and
   wherein the sealing plug is connected to the catching element, and wherein the sealing plug is removable from the outlet opening of the at least one reservoir by the movement of the catching element.

2. The discharging device according to claim 1, wherein the rotating element is rotatable about the rotary axis relative to the cartridge holder to a third orientation that differs from the first orientation and from the second orientation, and wherein the rotating element comprises at least one catch to take along into the third orientation a catching element of a cartridge held in the cartridge holder in order to open at least one outlet opening of the cartridge.

3. The discharging device according to claim 1, wherein the catching element is rotatable relative to the at least one reservoir in the direction of rotation of the rotating element.

4. The discharging device according to claim 1,
   wherein the at least one reservoir is designed as a flexible bag, and
   wherein at least one cutting element is connected to the catching element, which cutting element is arranged in such a manner that it cuts open the bag when the catching element is rotated, in order to form an outlet opening.

5. The discharging device according to claim 1, wherein the catching element forms a rigid unit together with the retaining element.

6. The discharging device according to claim 1, wherein the rotating element comprises a distal end wall, which comprises an insertion opening for the retaining element, which insertion opening is not rotationally symmetrical relative to the rotary axis, and wherein the retaining element comprises a form that is complementary to the form of the insertion opening so that the retaining element in the first orientation can be slid through the insertion opening into the rotating element, and subsequent rotation of the rotating element relative to the retaining element to the second orientation causes the retaining element to engage the end wall.

7. The discharging device according to claim 1,
   wherein the cartridge comprises at least two reservoirs that are arranged so as to be parallel, and
   wherein in the region of its respective distal end each reservoir comprises an outlet opening or an outlet region for forming an outlet opening.

8. The discharging device according to claim 1, wherein the rotating element comprises at least one stop element that interacts with the cartridge holder in order to on both sides delimit the range by which the rotating element can be rotated relative to the cartridge holder.

9. The discharging device according to claim 8, wherein the range by which the rotating element can be rotated relative to the cartridge holder is limited to less than 180°.

10. The discharging device according to claim 1, wherein in the region of its distal end the cartridge holder comprises a retaining flange, and wherein the rotating element comprises two half-shells that are slid onto the retaining flange across the direction of advancing and that are interconnected.

11. The discharging device according to claim 10, wherein the half-shells are at least in part enclosed by a rotating ring that is non-rotatably connected to the half-shells and that radially fixes the half-shells to each other.

12. The discharging device according to claim 1, comprising a restraining device that is designed in such a manner between the cartridge holder and the rotating element that for rotation of the rotating element it requires that a torque threshold be overcome.

13. The discharging device according to claim 1, comprising:
a handgrip that is rigidly connected to the cartridge holder, which handgrip extends essentially across the direction of advancing and is designed in such a manner that it can be held with at least two fingers of a hand of a user; and
a ball-of-the-thumb support provided on a proximal end of the advancing element, which ball-of-the-thumb support is designed in such a manner that by means of the ball of the same hand with which the user holds the handgrip said ball support can be advanced in the distal direction.

14. A discharging device for discharging at least one flowable component from a cartridge comprising at least one reservoir, comprising:
a cartridge holder;
at least one advancing element that is mounted on the cartridge holder and that is adapted to be axially advanced relative to the cartridge holder along a distal direction of advancing, which advancing element is configured to act on the at least one reservoir of the cartridge in order to dispense from the reservoir a component received in the reservoir; and
a rotating element that is mounted on the cartridge holder and is axially secured relative to the cartridge holder and is rotatable at least between a first orientation and a second orientation about a rotary axis that extends along the direction of advancing, wherein in the first orientation the rotating element makes it possible to axially insert the cartridge into the cartridge holder against the direction of advancing, and wherein the rotating element is configured to axially fix the cartridge inserted into the cartridge holder when it is in the second orientation,
wherein in the region of its distal end the cartridge holder comprises a retaining flange, and wherein the rotating element comprises two half-shells that are slid onto the retaining flange across the direction of advancing and that are interconnected.

15. The discharging device according to claim 14, wherein the half-shells are at least in part enclosed by a rotating ring that is non-rotatably connected to the half-shells and that radially fixes the half-shells to each other.

16. The discharging device according to claim 14, wherein the rotating element is rotatable about the rotary axis relative to the cartridge holder to a third orientation that differs from the first orientation and from the second orientation, and wherein the rotating element comprises at least one catch to take along into the third orientation a catching element of a cartridge held in the cartridge holder in order to open at least one outlet opening of the cartridge.

17. The discharging device according to claim 14, further comprising:
a cartridge with at least one reservoir for a component,
wherein the reservoir is designed in such a manner that the component can be dispensed from the at least one reservoir through an outlet opening by distal advancement of the advancing element, and
wherein the at least one reservoir is fixable in the cartridge holder so as to be essentially non-rotational.

18. The discharging device according to claim 17,
wherein the cartridge comprises a retaining element that relative to the at least one reservoir is axially secured in terms of the direction of advancing,
wherein the rotating element in the first orientation allows axial sliding of the retaining element into the rotating element, and
wherein the rotating element comprises a locking region which in the second orientation of the rotating element establishes a positive-locking connection or a non-positive-locking connection with the retaining element in relation to the distal direction of advancing.

19. The discharging device according to claim 18, wherein the rotating element comprises a distal end wall, which comprises an insertion opening for the retaining element, which insertion opening is not rotationally symmetrical relative to the rotary axis, and wherein the retaining element comprises a form that is complementary to the form of the insertion opening so that the retaining element in the first orientation can be slid through the insertion opening into the rotating element, and subsequent rotation of the rotating element relative to the retaining element to the second orientation causes the retaining element to engage the end wall.

20. The discharging device according to claim 14, wherein the rotating element comprises at least one stop element that interacts with the cartridge holder in order to on both sides delimit the range by which the rotating element can be rotated relative to the cartridge holder.

21. The discharging device according to claim 14, comprising a restraining device that is designed in such a manner between the cartridge holder and the rotating element that for rotation of the rotating element it requires that a torque threshold be overcome.

* * * * *